United States Patent [19]

Correia et al.

[11] Patent Number: 5,097,081

[45] Date of Patent: Mar. 17, 1992

[54] HYDRODECHLORINATION OF HIGHER CHLOROMETHANES

[75] Inventors: Yves Correia; Joseph Nowocien, both of Chateau-Arnoux, France

[73] Assignee: Atochem, Puteaux, France

[21] Appl. No.: 695,020

[22] Filed: May 3, 1991

[30] Foreign Application Priority Data

May 3, 1990 [FR] France .................. 90 05567

[51] Int. Cl.$^5$ .................. C07C 17/24; C07C 17/26; C07C 17/00; C07C 1/26
[52] U.S. Cl. .................. 570/101; 570/230; 570/257; 585/641
[58] Field of Search .................. 570/101, 230, 257; 585/641

[56] References Cited

U.S. PATENT DOCUMENTS

| | | | |
|---|---|---|---|
| 1,930,350 | 10/1933 | Strosacker et al. | 570/257 |
| 2,152,890 | 4/1939 | Kipper | 570/230 |
| 3,579,596 | 5/1971 | Mullin et al. | 570/101 |
| 4,157,380 | 6/1979 | Prahl | 570/101 |
| 4,983,783 | 1/1991 | Senkan | 585/641 |

*Primary Examiner*—J. E. Evans
*Attorney, Agent, or Firm*—Burns, Doane, Swecker & Mathis

[57] ABSTRACT

The highly chlorinated methanes, e.g., carbon tetrachloride, are improvedly dechlorinated by reacting same with hydrogen in the presence of oxygen or an oxygen-containing gas, e.g., air, and a catalytically effective amount of a metal of the copper or precious metal Groups of the Periodic Table, typically in the form of a fixed or fluidized bed thereof, and advantageously in the gaseous phase.

20 Claims, No Drawings

HYDRODECHLORINATION OF HIGHER CHLOROMETHANES

BACKGROUND OF THE INVENTION

1. Field of the Invention

The present invention relates to the dechlorination of highly chlorinated methanes, characteristically chloroform ($CHCl_3$) and carbon tetrachloride ($CCl_4$).

2. Description of the Prior Art

The syntheses of chloromethanes on an industrial scale are based on the chlorination of methane or of methyl chloride ($CH_3Cl$) and, as this reaction is simple, they are not completely selective. For example, it is not known in this art to produce methylene chloride ($CH_2Cl_2$) without concomitantly producing chloroform and carbon tetrachloride.

The chloromethanes are valuable intermediates and if, for example, only chloroform is required for a particular synthesis, the presence of the accompanying carbon tetrachloride becomes problematical. Need thus exists in this art for processes for the dechlorination of a chloromethane to convert same into a less highly chlorinated compound, or even into methane.

U.S. Pat. No. 3,579,596 describes reacting carbon tetrachloride or chloroform in the gas phase with hydrogen on a platinum catalyst. According to this '596 patent, the carbon tetrachloride is degraded to chloroform and methane. During such process, however, fouling of the catalyst and an instability of the reaction temperature are observed.

A similar reaction is described by Alvin H. Weiss, Baljit Singh Gambhir and Richard B. Leon in "Hydrodechlorination of carbon tetrachloride", *Journal of Catalysis*, 22, pages 245-254 (1971).

SUMMARY OF THE INVENTION

Accordingly, a major object of the present invention is the provision of an improved process for the dechlorination of highly chlorinated methanes by reaction with hydrogen in the presence of oxygen and a catalyst, such reaction being temperature-stable and which avoids fouling of the catalyst.

Briefly, the present invention features a process for the dechlorination of highly chlorinated methanes comprising reacting same with hydrogen, in the presence of oxygen and a catalytically effective amount of a metal of the copper Group or of a metal of Group VIII of the Periodic Table.

DETAILED DESCRIPTION OF THE PREFERRED EMBODIMENTS OF THE INVENTION

More particularly according to the present invention, the subject dechlorination of carbon tetrachloride to produce chloroform and methane, or of chloroform to produce methylene chloride and methane, is conducted quite readily. It is also within the scope of this invention to carry out a dechlorination of a mixture of highly chlorinated methanes. When the subject process is indeed carried out using such mixture, the bulk of the carbon tetrachloride is dechlorinated. Advantageously, the process of the invention is carried out employing a highly chlorinated methane in the gaseous phase.

In carrying out the process of the invention, either oxygen or a gas containing oxygen can be used, provided that the components of this gas, other than oxygen, are inert under the conditions of reaction. Air is advantageously used.

The catalyst may comprise a metal deposited onto suitable catalyst support. The metal is selected from among the metals of the copper Group of the Periodic Table, namely, copper, silver and gold, and from the precious metals of Group VIII, namely, ruthenium, rhodium, palladium, osmium, iridium and platinum; it may also comprise a mixture of such metals.

Advantageously, the support comprises aluminum and titanium dioxides having a specific surface area ranging from 20 to 300 $m^2$ per gram. The metal content typically ranges from 0.05% to 5%, preferably from 0.1% to 1% by weight of the total catalyst, i.e., the total weight of the metal and the support. The process of the invention may be carried out by passing a gaseous feedstream of chloromethane, hydrogen and oxygen (or air) over the catalyst in a fixed bed or in a fluidized bed. Simple cooling by means of a heat exchanger then suffices to separate (i) the unreacted hydrogen and oxygen (or air) and also the methane and hydrochloric acid (HCl) formed over the course of the reaction and (ii) the chlorinated hydrocarbons.

For example, if carbon tetrachloride is the starting material, the chlorinated hydrocarbons may be unreacted carbon tetrachloride, chloroform, methylene chloride, perchloroethylene ($C_2Cl_4$), hexachloroethane ($C_6Cl_6$) and methyl chloride ($CH_3Cl$). Some or all of these chlorinated hydrocarbons may then be separated and the carbon tetrachloride may then be recycled as a mixture with hydrogen and oxygen back into the process of the invention.

The reaction may be conducted under reduced pressure or under pressures equal or higher than atmospheric pressure, of up to 10 bar. The reaction temperature advantageously ranges from 30° to 350° C. and preferably from 100° to 250° C.

The molar ratio of $H_2$/highly chlorinated methanes is greater than one and preferably ranges from 1 to 10. The amount of oxygen, which may be supplied in the form of air, advantageously ranges from 0.01 to 5 mole % relative to the hydrogen. The residence time, defined as the ratio of the catalyst volume to the flow rate of the reagents hydrogen plus highly chlorinated methanes plus oxygen or gas containing oxygen, expressed under standard conditions (atmospheric pressure and 0° C.), advantageously ranges from 0.1 to 10 seconds and preferably from 0.5 to 5 seconds.

In order to further illustrate the present invention and the advantages thereof, the following specific examples are given, it being understood that same are intended only as illustrative and in nowise limitative.

EXAMPLES

A double-walled vertical glass tube reactor was selected; the inner tube had an internal diameter of 26 mm and a height of 850 mm. From the top of the reactor and extending downwardly, 600 mm of 5 mm × 5 mm glass rings, then 110 mm of catalyst and, finally, 60 mm of the above glass rings were arranged in the inner tube.

The reactor was charged with reagents from the upper end thereof. Three temperature probes were placed within the catalyst: T1 20 mm below the top level of the catalyst, T2 30 mm below T1, namely, 50 mm below the top level of the catalyst, and T3 50 mm below T2, namely, 100 mm below the top level of the catalyst. A condenser at −30° C. was placed at the reactor outlet in order to retain the chlorinated hydrocarbons; the gases were then washed with water to trap the HCl and, finally, the residual gases were transferred into an analyzer.

The above reactor was charged with a catalyst containing 0.5% of platinum deposited onto 125 m²/g alumina and a mixture of hydrogen, CCl₄ and air was introduced therein.

The operating conditions and the results obtained are reported in the following Table I.

As a comparative example, the procedure was also carried out in the following manner:

(a) the introduction of air was interrupted and a decrease in the degree of conversion of the carbon tetrachloride, a decrease in the productivity of the catalyst bed and an increase in the formation of perchloroethylene (PER) and hexachloroethane (Hexa) were observed. The operating conditions and the results obtained are also reported in Table I;

(b) using a fresh catalyst, an experiment was carried out under identical conditions, but in the absence of air. The operating conditions and the results obtained are reported in the following Table II.

From these experiments, it was determined that the addition of oxygen enabled fouling of the catalyst to be avoided and permitted better temperature control; the oxygen was almost completely recovered in the form of water.

In Tables I and II, the residence time is expressed as the ratio of the catalyst volume to the volume of the reagents H₂, CCl₄, O₂ and N₂ under STP standard conditions.

Also in the Tables, the temperature of the bath is the temperature of the fluid circulating in the double wall, the H₂/CCl₄ ratio is a molar ratio and air is expressed in % by volume of hydrogen introduced.

appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the dechlorination of a highly chlorinated methane, comprising reacting such highly chlorinated methane with a dechlorinating amount of hydrogen, in the presence of oxygen and a catalytically effective amount of a metal of the copper or precious metal Groups of the Periodic Table.

2. The process as defined by claim 1, said highly chlorinated methane comprising carbon tetrachloride.

3. The process as defined by claim 1, said catalytically effective metal being deposited onto a support substrate therefor.

4. The process as defined by claim 3, said support substrate comprising aluminum oxide or titanium dioxide and having a surface area ranging from 20 to 300 m²/g.

5. The process as defined by claim 4, said catalytically effective metal comprising from 0.05% to 5% by weight of the total weight of the catalyst.

6. The process as defined by claim 5, said catalytically effective metal comprising from 0.1% to 1% by weight of the total weight of the catalyst.

7. The process as defined by claim 1, carried out at a temperature ranging from 30° to 350° C.

8. The process as defined by claim 7, carried out at a temperature ranging from 100° to 250° C.

9. The process as defined by claim 1, carried out for from 0.1 to 10 seconds.

TABLE I

| Cumulative H₂ | Temperature Balances | | | | Reaction Conditions | | | Degree of conversion of CCl₄ | Production g/CCl₄ reacted/h bed/catalyst | Selectivity/CCl₄ reacted | | | | | |
|---|---|---|---|---|---|---|---|---|---|---|---|---|---|---|---|
| | Bath °C. | T1 °C. | T2 °C. | T3 °C. | H₂/CCl₄ Molar ratio | Air/H₂ % by volume | Residence time, seconds | | | HCCl₃ % | CH₄ % | CH₂Cl₂ % | PER % | Hexa % | CH₃Cl % |
| 9 | 38 | 169 | 73 | 42 | 8.3 | 2.5 | 1.75 | 80.1 | 1,190 | 59.6 | 37.8 | 1.3 | 0.4 | 0.06 | 0.53 |
| 13 | 60 | 145 | 85 | 62 | 8.4 | 0.56 | 1.79 | 72.3 | 1,062 | 67.7 | 30.1 | 1.05 | 0.5 | 0.3 | 0.37 |
| 83 | 60 | 160 | 95 | 65 | 8.65 | 5 | 1.72 | 33.6 | 1,048 | 58.2 | 38.6 | 1.07 | 0.09 | 0.03 | 1.96 |
| 111 | 60 | 160 | 97 | 67 | 8.2 | 5 | 1.71 | 72.2 | 1,085 | 57.7 | 38.9 | 1.06 | 0.08 | 0.07 | 2.27 |
| 156 | 60 | 159 | 95 | 66 | 8.5 | 5 | 1.72 | 71.5 | 1,035 | 57.5 | 39.4 | 0.95 | 0.08 | 0.05 | 2.01 |
| 204 | 60 | 157 | 93 | 66 | 8.4 | 5 | 1.72 | 70.1 | 1,030 | 58.1 | 38.7 | 0.77 | 0.03 | 0.06 | 2.39 |
| 259 | 60 | 158 | 92 | 66 | 8.5 | 5 | 1.72 | 70.2 | 1,019 | 57.6 | 38.3 | 0.8 | 0.03 | 0.05 | 2.5 |
| 300 | 60 | 158 | 91 | 66 | 8.6 | 5 | 1.72 | 70.3 | 1,010 | 57.1 | 39.1 | 0.9 | 0.07 | 0.05 | 2.9 |
| 325 | 120 | 153 | 151 | 130 | 8.3 | 0 | 1.79 | 83.4 | 1,235 | 72.0 | 25.0 | 0.9 | 1.93 | 0.19 | — |
| 372 | 118 | 130 | 133 | 138 | 8 | 0 | 1.79 | 48.2 | 743 | 77.2 | 18.5 | 0.68 | 1.77 | 1.84 | — |
| 392 | 140 | 140 | 152 | 155 | 8 | 0 | 1.79 | 42.7 | 657 | 68.3 | 22.6 | 0.93 | 3.69 | 4.45 | — |

TABLE II

| Cumulative H₂ | Temperature Balances | | | | Reaction Conditions | | | Degree of conversion of CCl₄ | Production g/CCl₄ reacted/h bed/catalyst | Selectivity/CCl₄ reacted | | | | |
|---|---|---|---|---|---|---|---|---|---|---|---|---|---|---|
| | Bath °C. | T1 °C. | T2 °C. | T3 °C. | H₂/CCl₄ Molar ratio | Air/H₂ % by volume | Residence time, seconds | | | HCCl₃ % | CH₄ % | CH₂Cl₂ % | PER % | Hexa % |
| 3.30 | 100 | 188 | 180 | 112 | 8.0 | 0 | 1.85 | 90.8 | 1,4718 | 68.7 | 28 | 1.95 | 1.3 | 0.05 |
| 21 | 100 | 154 | 162 | 123 | 8.0 | 0 | 1.85 | 90.5 | 1,409 | 74.7 | 23.4 | 1.4 | 0.5 | 0.03 |
| 48 | 90 | 115 | 102 | 94 | 8.0 | 0 | 1.85 | 34.1 | 517.2 | 80.8 | 16.1 | 0.2 | 1.0 | 1.9 |
| 69 | 120 | 157 | 158 | 160 | 8.0 | 0 | 1.85 | 87.7 | 1,317 | 73.5 | 23.8 | 1.3 | 1.38 | 0.14 |
| 93 | 120 | 148 | 147 | 153 | 8.0 | 0 | 1.85 | 78.1 | 1,203 | 75.8 | 21.3 | 1.0 | 1.4 | 0.33 |
| 117 | 120 | 144 | 140 | 145 | 8.0 | 0 | 1.85 | 63.9 | 1,000 | 77.81 | 19.2 | 0.73 | 1.5 | 0.76 |
| 141 | 130 | 153 | 149 | 152 | 8.0 | 0 | 1.85 | 58.5 | 939 | 73.16 | 20.5 | 0.86 | 3.08 | 2.45 |
| 166 | 130 | 148 | 143 | 142 | 8.0 | 0 | 1.85 | 40.8 | 653 | 73 | 21.5 | 0.30 | 2.47 | 2.8 |
| 189 | 160 | 176 | 173 | 170 | 8.0 | 0 | 1.85 | 35.8 | 594 | 55 | 25.5 | 1.36 | 5.9 | 12.22 |

While the invention has been described in terms of various preferred embodiments, the skilled artisan will 10. The process as defined by claim 1, wherein the molar ratio of hydrogen to said highly chlorinated methane is greater than 1.

11. The process as defined by claim 10, said molar ratio ranging from 1 to 10.

12. The process as defined by claim 10, wherein the molar ratio of oxygen to hydrogen ranges from 0.01% to 5%.

13. The process as defined by claim 1, said catalytically effective metal comprising copper, silver, gold, ruthenium, rhodium, palladium, osmium, iridium or platinum.

14. The process as defined by claim 13, said catalytically effective metal comprising platinum.

15. The process as defined by claim 1, carried out in the gaseous phase.

16. The process as defined by claim 1, wherein the oxygen is provided by a feedstream of air.

17. The process as defined by claim 1, said catalyst being present in the form of a fixed bed thereof.

18. The process as defined by claim 1, said catalyst being present in the form of a fluidized bed thereof.

19. The process as defined by claim 2, for the production of methane, chloroform, methylene chloride, perchloroethylene, hexachloroethane and methyl chloride.

20. The process as defined by claim 1, said highly chlorinated methane comprising chloroform.

* * * * *